(12) United States Patent
Lange et al.

(10) Patent No.: US 9,375,296 B2
(45) Date of Patent: Jun. 28, 2016

(54) METHOD FOR FABRICATING AN ABUTMENT

(75) Inventors: Gerlinde Lange, Langenselbold (DE); Horst Bachmann, Eschau (DE); Frank Fuchs, Reinheim (DE); Alexander Hilbert, Rodgau (DE)

(73) Assignee: DEGUDENT GMBH, Hanau (DE)

( * ) Notice: Subject to any disclaimer, the term of this patent is extended or adjusted under 35 U.S.C. 154(b) by 289 days.

(21) Appl. No.: 12/725,510

(22) Filed: Mar. 17, 2010

(65) Prior Publication Data

US 2010/0240012 A1    Sep. 23, 2010

(30) Foreign Application Priority Data

Mar. 20, 2009   (DE) .................. 10 2009 003 650

(51) Int. Cl.
*A61C 1/00* (2006.01)
*A61C 8/00* (2006.01)
(52) U.S. Cl.
CPC .............. *A61C 8/005* (2013.01); *A61C 8/0051* (2013.01); *A61C 8/0077* (2013.01)
(58) Field of Classification Search
CPC ............. A61C 8/08; A61C 2008/0084; A61C 8/00–8/0092
USPC ................. 433/215, 218, 201.1, 223, 72–75, 433/199.1, 167, 171–176; 264/16–19; 700/118–120, 180, 182
See application file for complete search history.

(56) References Cited

U.S. PATENT DOCUMENTS

| | | | |
|---|---|---|---|
| 5,417,572 A * | 5/1995 | Kawai et al. .................. 433/218 |
| 6,558,162 B1 | 5/2003 | Porter et al. | |
| 6,788,986 B1 | 9/2004 | Traber et al. | |
| 2001/0021498 A1 * | 9/2001 | Osorio et al. ................. 433/173 |
| 2002/0177108 A1 * | 11/2002 | Pavlovskaia et al. ......... 433/215 |
| 2003/0123943 A1 * | 7/2003 | Hamada .......................... 409/96 |
| 2004/0023188 A1 * | 2/2004 | Pavlovskaia et al. ......... 433/215 |
| 2007/0134625 A1 | 6/2007 | Leu et al. | |

(Continued)

FOREIGN PATENT DOCUMENTS

| | | |
|---|---|---|
| EP | 1518511 | 3/2005 |
| JP | 2000507866 A | 6/2000 |

(Continued)

OTHER PUBLICATIONS

Japanese Office Acton mailed Jan. 7, 2014, corresponding to Japanese Patent Application No. 2010-065618.
European Search Report, mailed Feb. 21, 2014, corresponding to European Application No. 10 15 5393.

*Primary Examiner* — Yogesh Patel
(74) *Attorney, Agent, or Firm* — Ladas & Parry LLP (57) ABSTRACT

A procedure for fabricating an individual abutment for a dental prosthesis for an implant anchored in an area of the jaw with an implant attachment running on the abutment side, using a working model molded by the jaw area equipped with the implant. The sulcus area of the gum uncovered above the implant and shaped by a sulcus-former extending from the implant attachment is reproduced in the working model. The abutment has a sulcus section running within the sulcus area and an adjoining head section to admit a part of a dental prosthesis. The sulcus area of the working model having an auxiliary implant attachment corresponding to the implant attachment is measured, and a sulcus section model determined with a circumferential surface and a de-facto sulcus line limiting it on the implant side.

24 Claims, 6 Drawing Sheets

(56) References Cited

U.S. PATENT DOCUMENTS

2007/0203600 A1* 8/2007 Shibata et al. ............... 700/98
2008/0220395 A1* 9/2008 Marshall et al. ............. 433/215
2009/0047629 A1 2/2009 Kim

FOREIGN PATENT DOCUMENTS

| JP | 2007075532 A | 3/2007 |
| WO | 2004060197 | 7/2004 |
| WO | 2008012597 A1 | 1/2008 |

* cited by examiner

METHOD FOR FABRICATING AN ABUTMENT

BACKGROUND OF THE INVENTION

The invention relates to a procedure for fabricating an individual abutment meant for a dental prosthesis for use in an implant anchored in an area of the jaw with an implant attachment on which the abutment is fixed or to which the abutment is aligned, using a working model molded by the jaw area equipped with the implant, with the sulcus area of the gum uncovered above the implant and shaped by a sulcus-former extending from the implant attachment being reproduced in the working model and with the abutment to be fabricated comprising a sulcus section running within the sulcus area and an adjoining head section to admit a part of a dental prosthesis, which if necessary is an integral component of the head section.

From EP-B-0 891 163 and EP-B-1 518 511, a dental prosthesis is known in which the abutment connecting an implant with a crown, which also can be designated as a post, is individually configured so that all the surfaces of the abutment projecting above the gum lines have a geometric course that corresponds to the surface of the externally visible part of the dental prosthesis, i.e., customarily a crown, though with smaller dimensions, since the abutment is provided with a cap or a facing.

With an implant-supported dental prosthesis according to EP-B-1 062 916, a working model of a jaw area to be equipped with a prosthesis is fabricated and, into the working model, a manipulation implant is inserted with auxiliary elements that then are scanned to determine base data that are used to determine interpolation data for a framework to be applied to the abutment or a superstructure surrounding the framework. For this, the abutment is individually configured, with an abutment blank to be processed being used, which can be adapted to what is needed with the least processing expense.

A dental prosthesis system is known from DE-B-10 2007 018 453. This comprises a dental implant and a superstructure built on it, which has a mounting post for mechanical support that can be individually produced.

The subject of WO-A-2004/060197 is a procedure for automatic generation of a dental superstructure for connecting with an implant. An inserted abutment can be optimized for shoulder width, stump height and turning angle.

Even if, as per the prior art, individually configured abutments are known, standard geometries are used for the section running below the gum line, without making allowance for the individual particulars of the jaw and gum area, in to which the dental prosthesis and thus the abutment are inserted.

SUMMARY OF THE INVENTION

The task that is the basis for the present invention is to develop a procedure of the type previously described so that the abutment is geometrically adapted or displayed in the area of it running below the gum line to the contour of the gum. It is especially to be ensured that the abutment and the gum are to be fitted so that deposits are avoided and the gum suffers no inflammation. The fabrication should also be simplified.

To solve the problem, in essence the invention makes provision that the sulcus area of the working model having an auxiliary implant attachment corresponding to the implant attachment is measured; that on the basis of the data obtained by the measurement, a sulcus section model is determined with a circumferential surface and a de-facto sulcus line limiting it on the implant side; that missing data between the determined auxiliary implant attachment or a zero-point area related to this and the de-facto sulcus line or an auxiliary sulcus line determined by interactive alteration of the de-facto sulcus line are supplemented by library data which are assigned to the sulcus-former; and that the data of the sulcus section model are used, while allowing for the de-facto sulcus line or the auxiliary sulcus line and the library data to produce the sulcus section.

According to the invention, especially through scanning, the sulcus area of the working model is measured so that then the measured data, thus point clusters, are converted into a triangulated surface model, so that the sulcus section model or sections of this is or are graphically represented. For this, individual points determined from the data are connected, and areas in which measurement data are missing are supplemented while making allowance for the measurement data determined or data from a library are allowed for, which fundamentally are assigned to the sulcus-former.

To make possible a clear allocation between the measured data (surface data) of the sulcus area and the library data of the sulcus-former or other required library data for producing the sulcus area of the abutment, first a so-called laboratory implant—also designated as an auxiliary implant—is inserted into the model, which from position and geometry corresponds to that of the implant in the jaw, to the extent the area is affected, which is necessary for positioning and attaching the abutment. Then the laboratory implant is equipped with an auxiliary element (measured element), which has an unambiguous geometric assignment to the laboratory implant and thus to the implant, ensuring that the orientation and position of the laboratory implant, and thus of the implant, are ensured in unambiguous fashion. The auxiliary element and the working model are measured and scanned jointly. It is not necessary that simultaneously the entire sulcus area be measured, to determine data for the sulcus section and thus the sulcus section model to be produced. Rather, for determination of the sulcus section model, beforehand the auxiliary element can be removed, so that the auxiliary element does not put parts of the sulcus area in shadow.

Since the sulcus-former inserted into the jaw also has a clear orientation and position vis-à-vis the implant, consequently the data of the sulcus-former stored in a library are to be clearly assigned to the measured data. Thus, all data are represented in a common coordinate system.

If necessary the type of implant used can be derived from the auxiliary element.

The sulcus line itself runs on the circumferential surface of the sulcus-former. For this, measurement data running on the implant side are determined as the initial measurement points that are connected with each other, with the de-facto sulcus line pre-set via the connection line. In determining the de-facto sulcus line, the library data on the sulcus-former are taken into account. The data are altered, either to automatically or interactively determine the auxiliary sulcus line, if measurement data would yield measured points that lie between the auxiliary implant attachment and the zero point area or even below the auxiliary implant attachment, with a shift of the de-facto sulcus line occurring on the circumferential surface of the sulcus-former to at least the zero point area like the zero point line or plane.

For the invention it is essential that the de-facto sulcus line, thus the lower limit line of the sulcus section model determined by the measurement, can be used as the initial point for individual configuration of the sulcus area of the abutment to be produced. The de-facto sulcus line basically runs above the zero point area which can be a surface or line, between which and the implant inserted in the jaw area, i.e. the implant attachment, which for example can be an implant shoulder. The abutment is not individually configured in this implant section, whose geometry is preset in fixed fashion and is designed to the structure of the implant, to ensure that the abutment—regardless of its otherwise individual configuration—is able to be inserted and attached into or onto the implant with an exact fit.

The zero point area of the abutment can be the underside of the abutment itself. However, customarily the implant section is cylindrical or tapered, with additional positioning elements provided on the end side like a hexagon, octagon, rhombus or an oval cylinder, which engage in form-locking fashion into a geometrically adapted section of the implant, securing it against twisting.

The jaw area is shaped when the inserted implant has grown in, the gum over the implant has been removed, and a sulcus-former is attached on the implant. After the sulcus-former has been attached on the implant over a preset time such as two weeks, it is removed, thus to produce a negative impression on the basis of which the working model is produced, which consequently represents the situation in the patient's jaw, in which the dental prosthesis is to be integrated.

From the measured or scanned data, not merely a de-facto sulcus line results, but also an emergence line that describes the gum line above which the abutment projects. Like the de-facto sulcus line, the emergence line can also be individually altered, to produce the sulcus section of the abutment based on the data that then are available.

The emergence line, which in actuality is a profile line, is determined directly from the measured or scanned data, whereby likewise—as with the de-facto sulcus line—individual secondary measurement points are determined from measurement data, that, connected with each other, define the emergence line. After the emergence line has been appropriately determined, its course can automatically be altered, especially shifted overall on the circumferential side by an interval d such as d≤0.5 mm in the direction of the implant. It is just as possible to shift it in the opposite direction.

If the de-facto sulcus line lies on the circumferential surface of the sulcus-former, the data of the de-facto sulcus line consequently are adjusted to those of the sulcus-former, then the emergence line runs outside the sulcus-former.

To form the envelopes of the sulcus section model, the first and second points which are equal in number are then connected with each other, without them crossing. The course of the connection lines is thus determined via the measured data of the sulcus area. The lines forming the envelopes then can be altered automatically or interactively in their course.

If the de-facto sulcus line is altered, then as a result of this the library share of the data that correspond to the sulcus-former, is increased. Especially if the sulcus line is elevated, i.e. shifted in the direction of the emergence line, the library share of the sulcus-former data is correspondingly increased.

Provision is especially made that the data determined by measurement of the sulcus area of the working model, and thus the surface model derived from the data in the form of the sulcus section model, are interactively altered so that the entire outer surface of the sulcus section model runs in radially convex and axially convex fashion or in a straight line. This ensures that in the abutment produced by the CAD-CAM technique, and particularly in its sulcus area, deposits do not build up between it and the gum.

Provision is especially made that the model is radially stretched, ensuring that the sulcus area of the abutment fully abuts on the gum. Consequently, an erasure of the gum mask is simulated, as occurs with the customary technique. Additionally, the data can be altered for smoothing the exterior surface of the sulcus area.

If measured data are present that lie below the zero point area, then according to the invention, as mentioned, provision is made that the de-facto sulcus line shifts in the direction of the zero point area, so that as a result, it is always ensured that the section of the abutment on the side of the implant is exactly adapted geometrically to the inserted implant.

Missing measured data between the de-facto sulcus line or the automatically or interactively altered de-facto sulcus line, which is designated as the auxiliary sulcus line, and the zero point area of the sulcus section are then supplemented by the data of the sulcus-former.

According to the invention, the sulcus area of the abutment is individually configured, thus the part of the abutment is limited toward the upper part, i.e. the head section, by the emergence line or the emergence profile and toward the lower part by the zero point area.

The sulcus section of the abutment can be exactly adjusted automatically corresponding to the measured sulcus area in the working model and smoothed to the required extent. Especially provision can be made for an automatic smoothing while allowing for the emergence line or the emergence profile and of the zero point area.

The geometric data determined from the measured data can be automatically altered, which represent the sulcus area in such a way that a completely convex geometry results with a simultaneous smoothing of the surface.

Additionally the sulcus area can be expanded or enlarged. This can be done particularly in the area of the emergence line, so that the abutment produced by the CAD-CAM technique fully adjoins the gum.

Missing data are supplemented by those of the sulcus-former used, i.e., its geometric information and circumferential geometry data are included. If—as in the emergence profile area—there is no adaptation to the sulcus-former, the missing data are supplemented via suitable algorithms.

BRIEF DESCRIPTION OF THE DRAWINGS

Further particulars, advantages and features of the invention are drawn not merely from the claims, and the features to be gleaned from then—by themselves and/or in combination—, but also from the following description of an embodiment example shown in the drawings.

Shown are.

DESCRIPTION OF THE PREFERRED EMBODIMENTS

Figure 1:
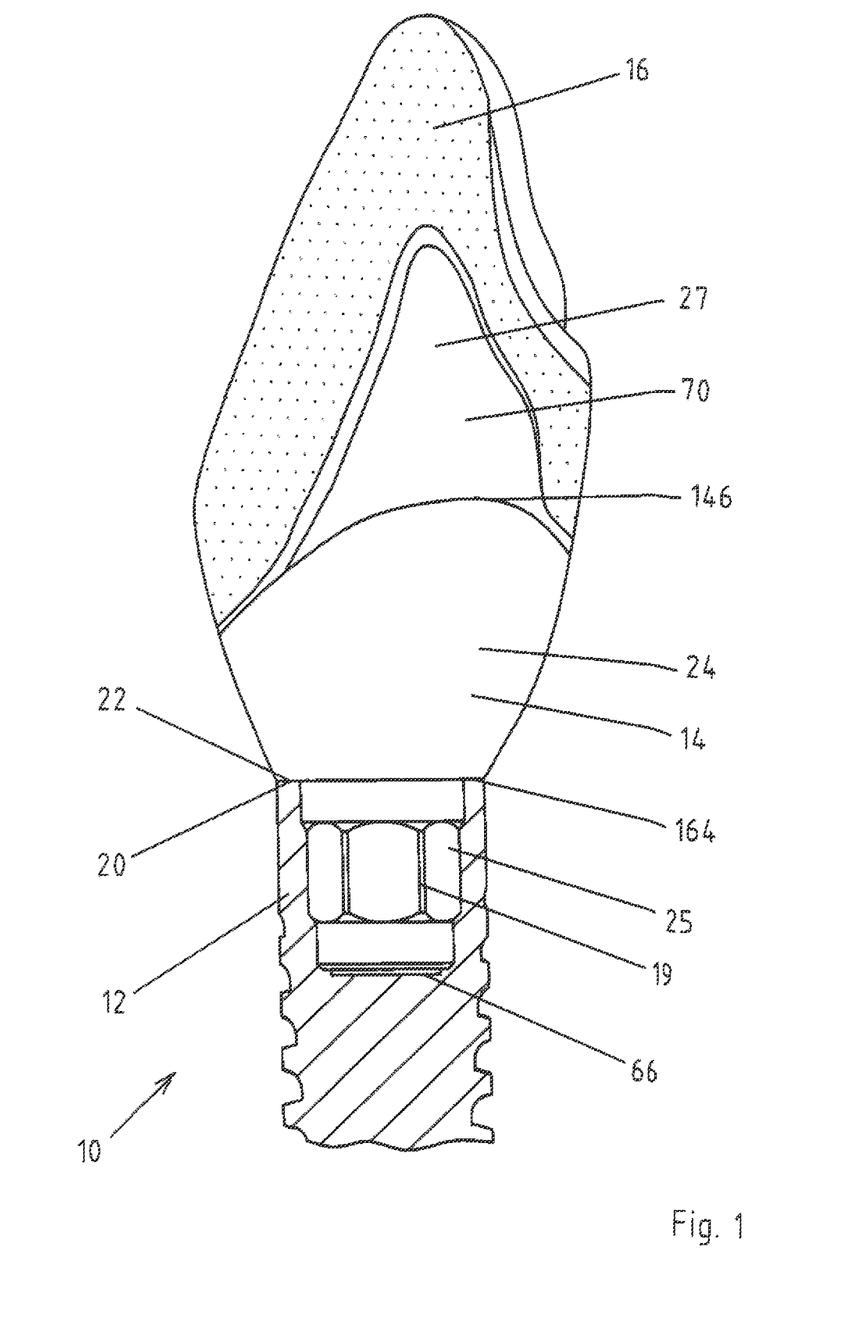
FIG. 1: a dental prosthesis.

FIG. 1 shows, purely in principle, a dental prosthesis 10 which is to replace a front tooth. The dental prosthesis 10 consists of an implant 12, preferably capable of being screwed in, in the area of the jaw in which the front tooth is to be replaced; an abutment 14, that can be inserted in form-locked and non-twisting fashion into implant 12, and is able to be connected with it; and a faced crown 16. Regarding the principal design of dental prosthesis 10, reference is made however to structures sufficiently known, so no need exists for more comprehensive explanations. Therefore also, no details are provided either regarding a positioning device or positioning elements which are provided in both the implant 12 and the abutment 14.

In fact from the principle depiction of FIG. 1, a hexagon 19 is perceptible as the positioning device, which engages into a receptacle with an appropriately adapted geometry in implant 12.

The implant 12 has a shoulder 20 on which an encircling band 22 of abutment 14 sits when properly positioned. Abutment 14 itself is connected with implant 12 by means of a screwed element that is not depicted in greater detail and which penetrates implant 14 in the direction of the longer axis. For this, implant 12 has a blind hole with an appropriate interior threading, this not able to be gleaned from the drawing.

According to the invention, abutment 14 is individually configured, at least in a so-called sulcus section 24, which is surrounded by the gum when abutment 14 is secured. On the implant side, sulcus section 24 makes a transition into an implant section 25, the geometry of which is preset by the implant inserted in the jaw, thus independent of the otherwise individual configuration of abutment 14. Additionally, on the head side, sulcus section 24 makes a transition into a head section 27, which is surrounded by the facing crown 16.

The dividing line between head section 27 and sulcus section 24 is delimited by a so-called emergence line 146. Emergence line 146 is directed to the upper edge of the gum space, above which the head section 27 of abutment 14 projects. If necessary, after it is determined, emergence line 146 can be shifted in the direction of implant 12 or head section 27.

A so-called zero point area divides sulcus section 24 from implant section 25. In the graphic depiction of FIG. 1, the band 22 runs in the zero point area. To appropriately configure sulcus section 24 to the surrounding conditions in the jaw in which dental prosthesis 10 is inserted, the procedure according to the invention is as follows.

In a known manner, first after removal of the tooth to be replaced, an implant is inserted into the patient's jawbone. After the implant has grown into the bone, the gum tissue covering the implant is opened, to insert a so-called sulcus-former. After this has been in the gap in the teeth over a time that complies with an experience value, such as two weeks, it is removed, to produce by modeling of the jaw in this area a negative impression, from which a working model 26 is produced that reflects the situation in the patient's jaw in which the dental prosthesis is inserted.

Figure 2:
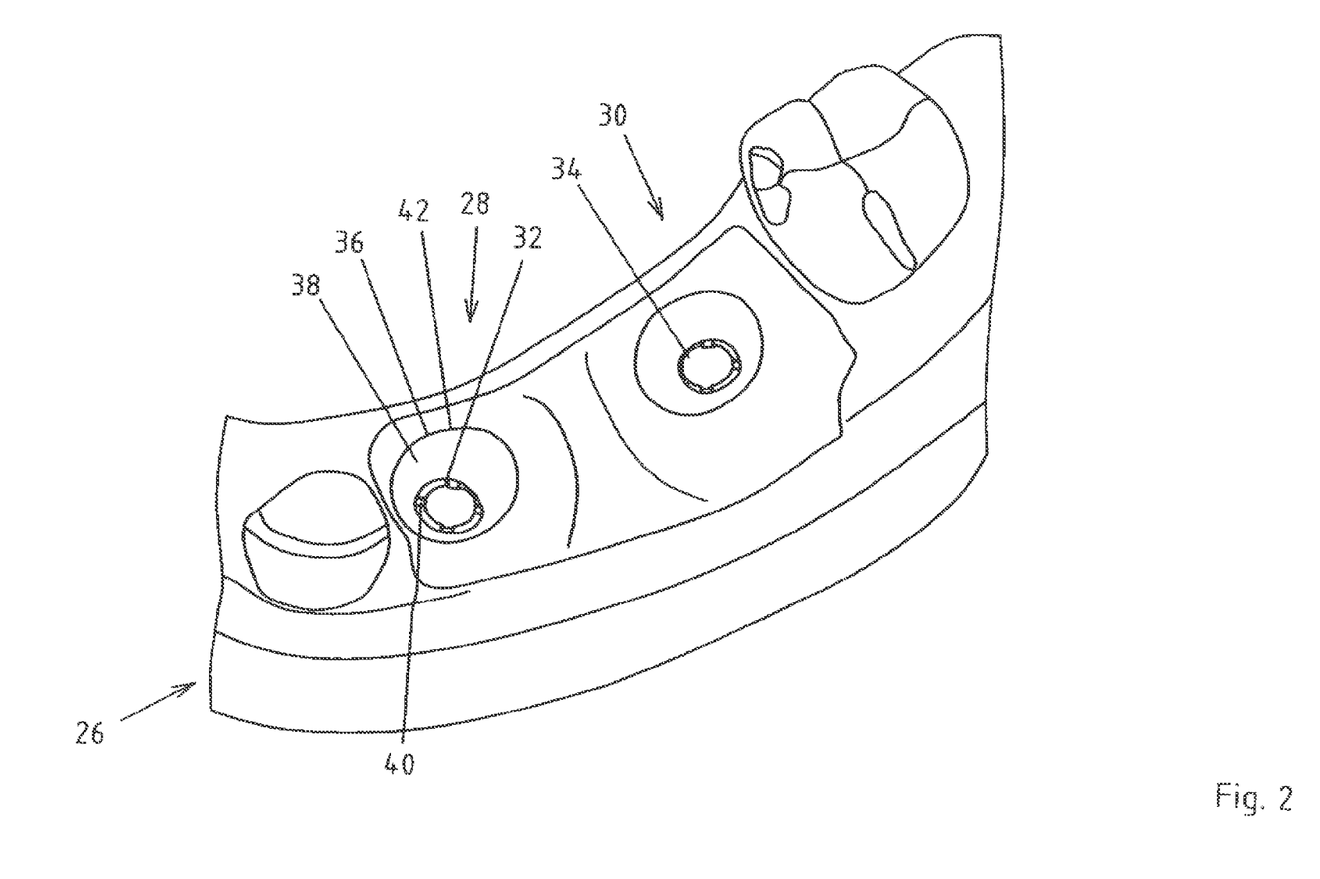
FIG. 2: a working model.

In FIG. 2, the working model 26 has two gaps 28, 30 into which a dental prosthesis is integrated. Additionally, working model 26 is processed by a dental technician to the point where so-called laboratory implants 32, 34 are inserted in working model 26, which are identical in orientation and position to the implants that are used in the jaw. The area of the laboratory implants 32, 34 on which an abutment sits or to which the abutment assumes a fixed preset position, which is designated by the implant as an implant attachment and by the laboratory implant as an auxiliary implant attachment, is the visible outer surface of the implant or of the laboratory implant.

Then the gaps 28, 30 are measured, to determine data for the area of the abutment that runs inside the sulcus area. This is explained purely by way of example using FIGS. 3 to 5.

Thus, for example, the gap 28 with a realistically reproduced area 36 that surrounds gap 28 in the embodiment example, is scanned or measured by some other suitable procedure. In a first measurement step, an auxiliary element—also called a scanning aid—is inserted into laboratory implant 32, the position and orientation of which coincides with the realistic implant that is inserted into the jawbone, which [auxiliary element] has a defined orientation to the auxiliary implant 32, so that the measured data reflect the position and orientation of the implant in the jaw area.

Since the sulcus-fomer used in the implant also has a clear orientation and position vis-à-vis the implant, consequently the sulcus-former data stored in a library can be clearly related to the laboratory implant data and thus that of the real implant, so that as a result, measured data of the sulcus area of the imprint, i.e. of area 36, which runs between the upper side or shoulder 40 of laboratory implant 32, i.e. the auxiliary implant attachment, and the upper limit of the area 36 surrounding gap 28, can be unambiguously correlated to the implant in terms of coordinates. The data on the implant, the sulcus-former and that of the sulcus area of the working model, and thus on the gum that surrounds the gap, can be depicted consequently in a common coordinate system, the origin of which is designated in FIG. 4 as zero point 43.

To be able without shadings to measure, when scanning sulcus area 38 of working model 26, i.e. of the area that surrounds gap 28, that extends between the shoulder 40 designated as an auxiliary implant projection, to upper edge 42 of area 36, usually the auxiliary element is removed, after this has been previously measured with proper positioning in the laboratory implant 32 together with the relevant area of working model 26, i.e. at least with coverage of the auxiliary implant projection and of area 26 with the upper edge 42 that delimits it.

Figure 3:
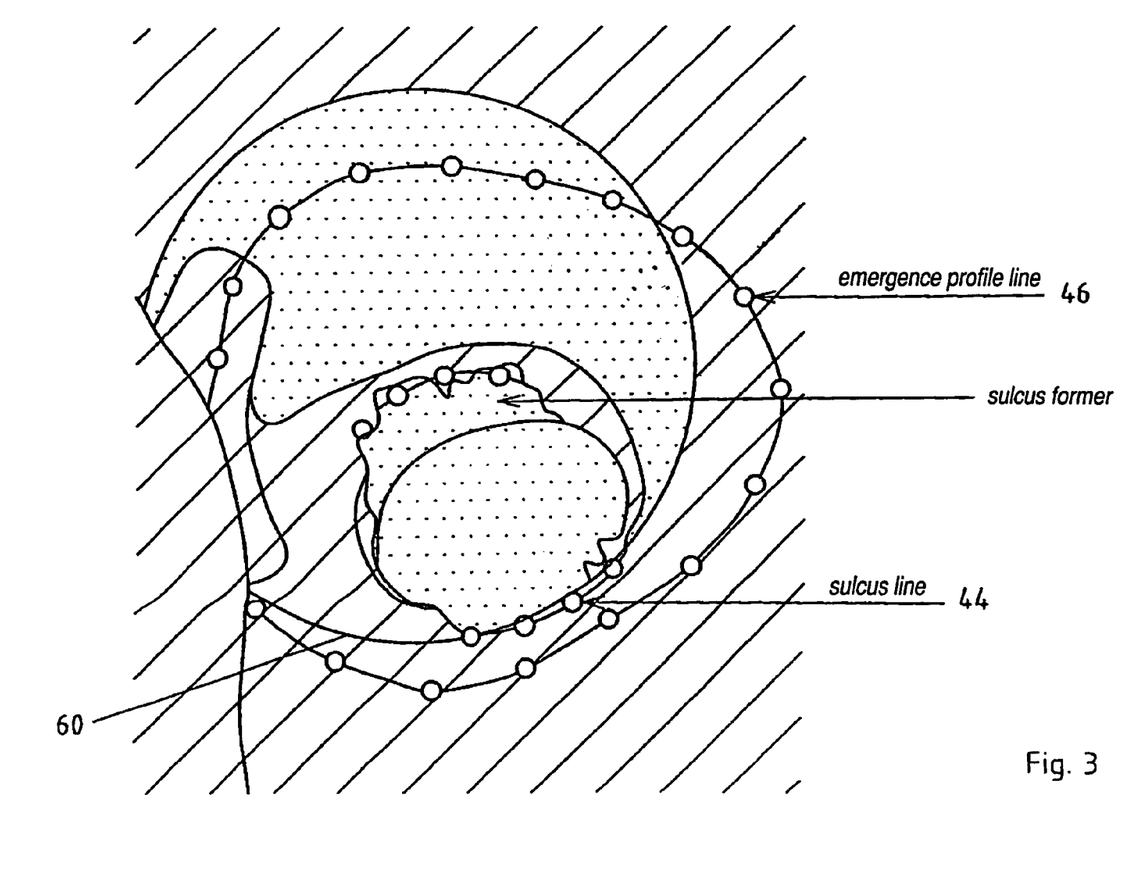
FIG. 3: an image with measurement points, determined by scanning a gap in the working model in FIG. 2.
Figure 4:
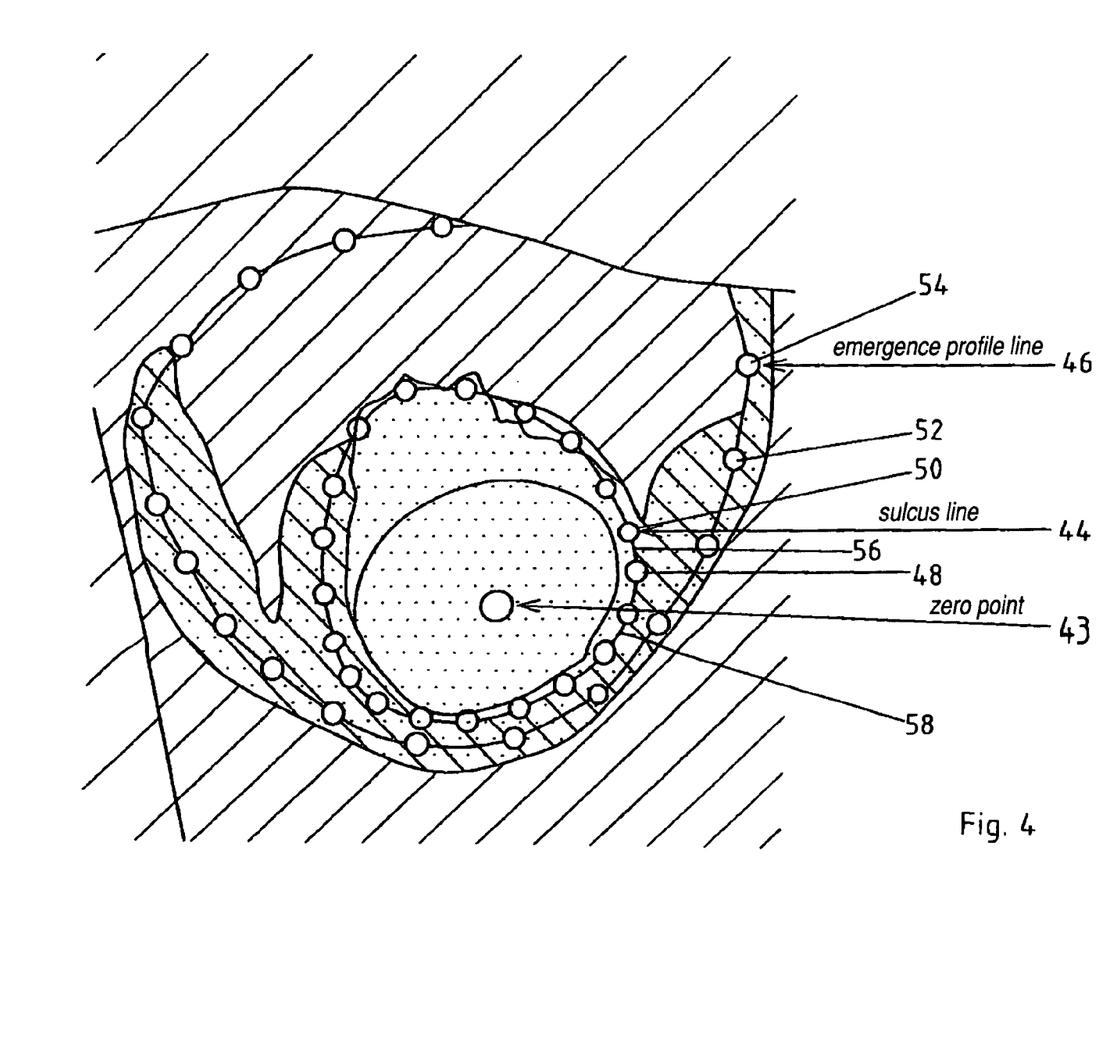
FIG. 4: another depiction of the gap in the working model as per FIG. 2 with a superimposed sulcus-former.

The point clusters determined by measurement such as scanning are then converted into graphically depicted surface data as is shown in FIGS. 3 and 4. The measurement data that have been obtained by scanning gap 28, are delimited by two lines characteristic of the gap, that are determined from the measurement data.

As FIG. 4 shows, a sulcus line 44 and an emergence profile line 46 are generated from the measured data. Emergence profile line 46 is determined by the upper edge of the area 36 surrounding gap 28. Correspondingly, from the lower measured data, i.e. those situated closest in relation to laboratory implant 32, the sulcus line 44 is determined. Both sulcus line 44 and emergence profile line 46 are formed from measurement points 48, 50 or 52, 54 determined from the measured data and connected with each other. Measurement points 48, 50 of sulcus line 44 are designated as the first measured points, and measured points 52, 54 of emergence profile line 46 as the second measured points. The first measured points 48, 50 and the sections 56, 58 that join them to form sulcus line 44 are modified that in terms of the data they come to lie on the circumferential surface of the sulcus-former, the data for which are stored in a library. This is principally made clear by FIG. 3. One can recognize sulcus line 44, which lies on the circumferential surface 60 of a depicted sulcus-former 62.

Figure 5:
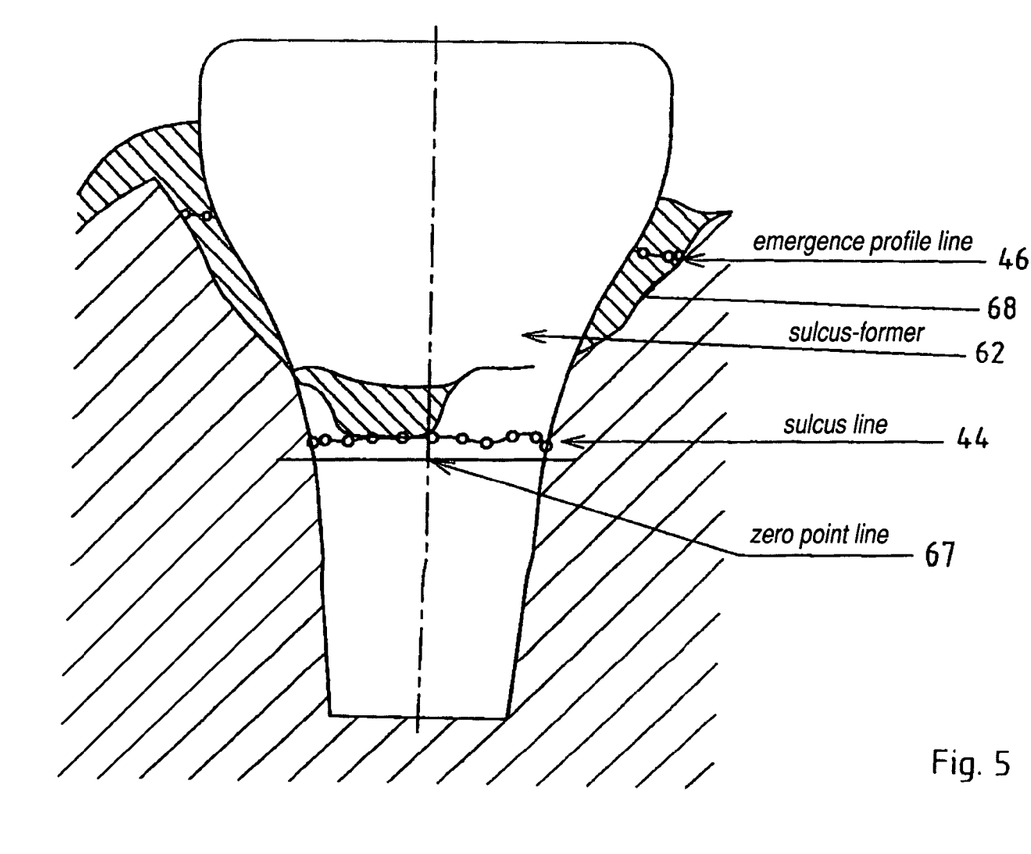
FIG. 5: a depiction of measurement data with superimposed sulcus-former.
Figure 6:
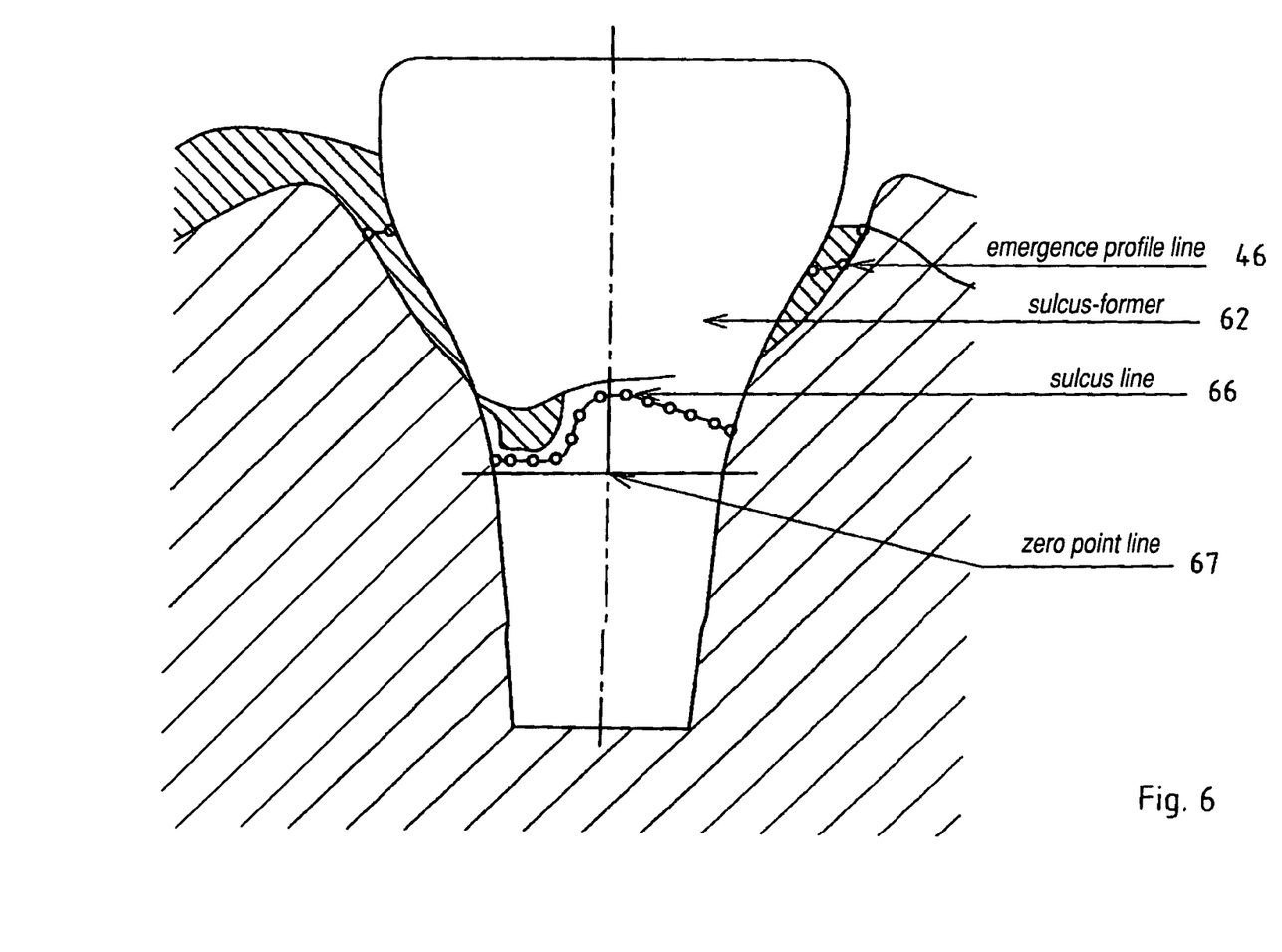
FIG. 6: a depiction corresponding to FIG. 5 with individually altered data.

The corresponding sulcus-former 62 is also depicted in FIGS. 5 and 6. The emergence profile line 46, which follows the height profile of the upper gum line into which the dental prosthesis is inserted, and thus the edge 42 in working model 26, runs on the other hand at a distance to the sulcus-former 62. Missing measured data are determined while taking into account adjoining measured data and with a suitable algorithm as a basis. In regard to sulcus line 44, missing data are supplemented by surface data of sulcus-former 62.

Sulcus line 44 is determined by data that are still determined from scanning of area 36 that surrounds gap 28. Normally sulcus line 44 runs at a distance to zero point line 67 drawn in FIG. 6, below which the abutment to be produced must reveal fixed, preset geometry values in order to be inserted with a precise fit into the implant. Zero point 67 would correspond to band 22 in FIG. 1. Consequently, from band 22 to the lower end 66 of abutment 14, recourse was had to library data that are not altered, through which it is ensured that notwithstanding the individual configuration of sulcus area 24 of abutment 14, the abutment 14 is inserted as per position and with exact fit into implant 12.

The data missing between sulcus line 44 and zero point line 67 are then supplemented by data of sulcus-former 62 stored in the library.

As a comparison between FIGS. 5 and 6 makes clear, a possibility exists to shift sulcus line 44 individually. As per FIG. 6, a section of sulcus line 44 in FIG. 5 has been shifted in the direction of emergence profile line 46. Sulcus line 66 thus altered nonetheless continues to run on the surface of sulcus-former 62.

From FIGS. 5 and 6 it also becomes clear that sulcus-former 62 runs in its upper area at a distance to a an area 68 designated in dentistry terms in the actual sense as a sulcus or to the area 36 surrounding gap 28 in the embodiment example of FIG. 2.

To obtain data for the envelope of the sulcus section of abutment 14 designated by 24 in FIG. 1, the first measured points 48, 50 are connected with the second measured points 52, 54, with the contour of the connecting lines determined from the scanned data of so-called sulcus area 38 in working model 26, which is preset by the contour of the gum that runs between emergence line 46 and zero point line 64. In this way, data for a sulcus section model are generated that are needed to produce sulcus section 24 in CAM technology.

According to the invention, a possibility exists to configure sulcus section 24 individually not just by altering sulcus line 46 in its progression, but rather the surface data of the sulcus section model determined from the measured data can also be altered to the degree that the surface is smoothed. With this, in supplemental fashion and in an emphasized configuration, provision is made that the surface is altered so that it runs with its full extent in convex fashion in the axial direction, if necessary with straight-line sections, and is basically convex radially. However, this does not preclude obtaining locally concave surface areas when computing the sulcus section model that are not smoothed, so that sulcus section 24 produced using CAD-CAM technology has appropriate indentations.

Provision especially is made that the sulcus section model produced from the measured data while making allowance for the library data of the sulcus-former 62, from which the sulcus section 24 is produced using CAD-CAM technology, is expanded in the area of emergence profile line 46, so that as a consequence sulcus section 24 fully adjoins the gum in the area where the abutment emerges from the gum line.

In addition, in a preferred manner, the contour of emergence profile line 46 is altered to the extent that the emergence profile line needed to construct sulcus section 24 is shifted in the direction of the sulcus line. Thus, the emergence profile line taken into account for production of sulcus section 24 can run, for example, at an interval of up to 0.5 mm to the measured emergence profile line.

In FIG. 1, the emergence line allowed for in producing sulcus section 24 is designated by reference symbol 146 and the zero point line by the reference symbol 164, which coincides with the surrounding band 20.

The upper section or head section 70 of abutment 14 surrounded by the facing crown 16 can also be individually configured. For this provision is made that a physical wax up is inserted into gap 28, that corresponds to the tooth to be replaced from the outer configuration. This is followed a scanning to determine the surface geometry. This surface geometry is reduced while allowing for the thickness of the facing crown 16, to determine the surface geometry of head section 70 of abutment 14 on the basis of these data. Thus, the facial and/or buccal and/or mesial and/or distal and/or lingual and/or occlusal surface of head section 70 can geometrically follow the contour of the corresponding outer surfaces of facing 18.

Abutment 14 itself is produced from a blank or a semi-finished product. An appropriate blank or semi-finished product can already have implant section 25 as a prefabricated section.

What is claimed is:

1. A method for producing an individual implant abutment for a dental prosthesis, the method comprising the steps of:
   anchoring an implant into a jaw area of a patient;
   inserting a sulcus former into the jaw area;
   forming a sulcus in the jaw area using the sulcus former;
   removing the sulcus former;
   taking an impression of the sulcus area using the sulcus former;
   producing a working model, based on the impression, to reflect a condition in the jaw area with the dental prosthesis;
   processing the working model by inserting an auxiliary implant corresponding identically in orientation and position to the implant anchored in the jaw area;
   measuring the sulcus area of the working model;
   generating a sulcus section model, based on the measured sulcus areas, with a circumferential surface and a de-facto sulcus line limiting said circumferential surface on an implant side;
   supplementing data, which is missing in a first region between a connection of the auxiliary implant, or a related zero-point area, and the de-facto sulcus line, or an auxiliary sulcus line defined by shifting the de-facto sulcus line, by first library data corresponding to data of a region of the sulcus former running in the first region; and
   generating a sulcus section model based on measurements of the sulcus area, on the de-facto sulcus line or the auxiliary sulcus line, on the first library data, on the auxiliary implant connection, and on the zero point area.

2. The method according to claim 1, comprising:
   determining first measurement points from measurement data on the sulcus area of the working model close to the implant side;
   forming a de-facto sulcus line from a connection of said first measurement points to each other, wherein both the first measurement points and the de-facto sulcus line lie on a surface of the sulcus-former; and
   in a situation where the first measuring points and the de-facto sulcus line do not lie on the surface, modifying data of the first measuring points and de-facto sulcus line so that the first measuring points and de-facto sulcus line lie on the surface.

3. The method according to claim 1, comprising adjusting the data on an auxiliary implant attachment and the data on the sulcus-former to each other by means of an auxiliary element conveying the position and orientation of the implant.

4. The method according to claim 3, comprising inserting into the implant an auxiliary element derived from the auxiliary implant used in the working model.

5. The method according to claim 1, comprising defining an emergence line of the abutment following an upper boundary of a sulcus area modeled on the gum in the working model or running below the upper boundary at a distance d with d≤0.5 mm.

6. The method according to claim 5, comprising supplementing measured data for determining the emergence line by library data.

7. The method according to claim 5, comprising setting the emergence line so that the emergence line runs above a measured upper boundary of the sulcus area.

8. The method according to claim 5, wherein a number of second measurement points geometrically determine the emergence line, and a number of first measurement points geometrically determine the de-facto or auxiliary sulcus line, comprising choosing as equal the number of the first and second measurement points.

9. The method according to claim 8, comprising joining the first and second points via non-intersecting connection lines that preset an envelope of the sulcus section model.

10. The method according to claim 9, comprising defining the contour of the connection lines from the measured data of the sulcus area.

11. The method according to claim 10, comprising automatically or interactively altering the connection lines.

12. The method according to claim 1, comprising automatically or interactively altering the sulcus section model relative to at least one of the de-facto sulcus line and the emergence line.

13. The method according to claim 1, comprising automatically or interactively altering data on the circumferential surface of the sulcus section model, so that the circumferential surface, considered axially in circumferential fashion, runs convex or in a straight line.

14. The method according to claim 13, comprising automatically smoothing the circumferential surface of the sulcus section model.

15. The method according to claim 1, comprising automatically or interactively altering data on the circumferential surface of the sulcus section model, so that, viewed circumferentially and radially, the circumferential surface runs convex.

16. The method according to claim 1, comprising determining the zero point area through secondary library data; and
shifting measured points of the de-facto sulcus line lying between the zero point area and the auxiliary implant attachment to the zero point area or to a zero point line preset by said zero point area.

17. The method according to claim 1, wherein an implant section of the abutment to be connected with the implant adjoins the sulcus section, said implant section being preset depending on the implant used.

18. The method according to claim 1, wherein the measuring is carried out by scanning.

19. The method according to claim 1, comprising converting data of the sulcus area into triangulated surface points using a microprocessor, and graphically depicting the triangulated surface points on a computer monitor.

20. The method according to claim 19, comprising connecting the triangulated surface points with each other for forming surface models.

21. The method according to claim 1, comprising replacing missing measured data by library data.

22. The method according to claim 21, comprising replacing missing measured data in areas of the sulcus-former.

23. The method according to claim 1, comprising selecting a surface of the head section of the abutment from the group consisting of a facial surface, a buccal surface, a mesial surface, a distal surface, and an occlusal surface, and configuring said surface of the head section so that the surface follows the contour of said surface of the dental prosthesis part visible from the outside.

24. The method according to claim 1, comprising shaping the jaw area when the implant anchored in the jaw area has grown in, removing gingiva over the implant, and then inserting the sulcus former.

* * * * *